United States Patent
Chordia et al.

(10) Patent No.: US 7,905,133 B2
(45) Date of Patent: Mar. 15, 2011

(54) VARIABLE RATIO FLOW SPLITTER FOR A FLOWSTREAM

(75) Inventors: Lalit Chordia, Pittsburgh, PA (US); Kimber D. Fogelman, Hockessin, DE (US); Edwin E. Wickfors, Landenberg, PA (US); James L. Waters, Framingham, MA (US)

(73) Assignee: Thar Instruments, Inc., Pittsburgh, PA (US)

( * ) Notice: Subject to any disclaimer, the term of this patent is extended or adjusted under 35 U.S.C. 154(b) by 475 days.

(21) Appl. No.: 12/152,785

(22) Filed: May 16, 2008

(65) Prior Publication Data

US 2009/0165873 A1 Jul. 2, 2009

Related U.S. Application Data

(60) Provisional application No. 61/009,423, filed on Dec. 28, 2007.

(51) Int. Cl.
*G01N 1/18* (2006.01)
*G01N 1/00* (2006.01)

(52) U.S. Cl. ..................................................... 73/61.56

(58) Field of Classification Search .................. 73/61.56
See application file for complete search history.

(56) References Cited

U.S. PATENT DOCUMENTS

| | | | |
|---|---|---|---|
| 5,108,466 A | 4/1992 | Klein et al. | |
| 6,106,710 A | 8/2000 | Fischer et al. | |
| 6,289,914 B1 | 9/2001 | Tommasi | |
| 6,296,020 B1 * | 10/2001 | McNeely et al. | 137/806 |
| 6,402,946 B1 | 6/2002 | Spraul et al. | |
| 6,406,633 B1 | 6/2002 | Fischer et al. | |
| 6,413,428 B1 | 7/2002 | Berger et al. | |
| 6,413,431 B1 | 7/2002 | Abedi | |

(Continued)

FOREIGN PATENT DOCUMENTS

EP 0544988 A1 6/1993

OTHER PUBLICATIONS

Pinkston, Advantages and drawbacks of popular supercritical fluid chromatography/mass spectrometry interfacing approaches—a user's perspective, Mar. 31, 2005, Eur, J. Mass Spectrom, vol. 11, pp. 189-197, Mason, OH.

(Continued)

*Primary Examiner* — Hezron Williams
*Assistant Examiner* — Rodney T Frank
(74) *Attorney, Agent, or Firm* — Debra Z. Anderson

(57) ABSTRACT

A splitter for a pressurized primary flowstream of a mobile phase is provided. The splitter comprises a first splitting stage that divides the primary flowstream between a major split flowstream and a minor split flowstream by means of a first and a second restrictive flow element; a first dilution stage that combines a dilution flow source with the minor split flowstream to create a diluted minor flowstream; a second splitting stage that divides the diluted minor flowstream between a secondary major diluted flowstream and a secondary minor diluted flowstream by means of a third restrictive element in the secondary minor diluted flow stream; and a second dilution stage wherein a conditioning flow source conditions the secondary minor diluted flow stream after the third restrictive element prior to outlet of the secondary minor diluted flowstream from the splitter.

18 Claims, 3 Drawing Sheets

U.S. PATENT DOCUMENTS

| | | | |
|---|---|---|---|
| 6,458,273 B1 | 10/2002 | Krakover et al. | |
| 6,601,613 B2 * | 8/2003 | McNeely et al. | 137/833 |
| 6,767,467 B2 | 7/2004 | Fischer et al. | |
| 6,817,554 B2 | 11/2004 | Gangl et al. | |
| 6,880,576 B2 * | 4/2005 | Karp et al. | 137/806 |
| 6,890,489 B2 | 5/2005 | Nichols et al. | |
| 6,908,557 B2 | 6/2005 | Chordia et al. | |
| 6,911,092 B2 * | 6/2005 | Sneh | 118/715 |
| 6,997,031 B2 | 2/2006 | Gilby et al. | |
| 7,086,279 B2 | 8/2006 | Gilby et al. | |
| 7,635,502 B2 * | 12/2009 | Sneh | 427/248.1 |
| 2002/0121468 A1 | 9/2002 | Fischer et al. | |
| 2006/0078986 A1 * | 4/2006 | Ly et al. | 435/287.2 |
| 2007/0263477 A1 * | 11/2007 | Sudarsan et al. | 366/3 |

OTHER PUBLICATIONS

Xiang, et al., A New Reference Correclation for the Viscosity of Methanol, Nov. 8, 2006, J. Phys. Chem. Ref. Data, vol. 35, No. 4, 2006, pp. 1597-1620, Boulder, CO.

QuickSplit Flow Splitters, catalog, http://www.hplc-asi.com, available Dec. 3, 2003 in PDF format from the website.

Cai, et al., A straightforward means of coupling preparative high-performance liquid chromatography and mass spectrometry, Rapid Commun. Mass Spectrom, 2002; 16: 544-554.

Zhang, et al., A systematic investigation of recovery in preparative reverse phase high performance liquid chromatography/mass spectrometry, Journal of Chromatography A. 1119, (2006)147-155.

* cited by examiner

VARIABLE RATIO FLOW SPLITTER FOR A FLOWSTREAM

CROSS-REFERENCE TO RELATED APPLICATION

This application claims priority under 35 U.S.C. §119(e) to provisional application Ser. No. 61/009,423, filed Dec. 28, 2007, incorporated by reference in its entirety.

FIELD OF THE INVENTION

This invention relates to flow splitters for use in fluidic systems including chemical instrumentation systems such as chromatographic, extraction and reaction systems.

BACKGROUND OF THE INVENTION

Subdivision of flowstreams into two or more paths is a frequent requirement in modern chemical instrumentation. The apparatus used to create the separate flowstreams is generally referred to as a flow splitter. Frequently flow splitters are used to present some representative portion of the output of a flow system to an electronic detector, typically to measure the progress of some chemical processing step [e.g. separation, extraction or reaction progress].

Analytical liquid chromatography is used for separation of complex mixtures of solutes dissolved in a liquid solvent. A high pressure pumping system is used to force a liquid mobile phase through a separation column packed with very small, high surface area silica spheres that have been chemically modified to interact at differing degrees with different types of solutes. A strong interaction between the modified silica surface and a solute will cause the solute to be retained at the surface for a longer period than a weak interaction. Thus, for a mixture of solutes, those having a weaker interaction with the silica surface will emerge from the separation column in a shorter period of time than those with strong interactions.

The liquid mobile phase also plays a significant role in the time a particular solute spends on the separation column. Weak solvents are those that are unable to remove solutes from the separation surface. Strong solvents are those that readily redissolve solutes that are even strongly adsorbed on the surface. For a mixture with a wide range of solutes that interact differently, a technique called gradient elution is used. In this case, the original mobile phase starts at a composition that makes it a very weak solvent. Gradually, the composition is changed by increasing the relative concentration of strong solvent. The process continues until a maximum composition is reached or all solutes have been eluted from the column.

The result is that a complex mixture of solutes introduced to a separation column emerge as individual solutes at different times and in different flow segments of the mobile phase based on the strength of their interaction with the modified silica surface and the mobile phase. With the solutes separated into different flow segments of the mobile phase flowstream, the flow can be directed through an electronic detector which can sense presence of specific types of solutes based on the solutes' physical properties [e.g. molecular mass, UV-visible light absorption, refractive index, electrochemical reduction or oxidation potential, etc.]. Such detectors generate an electronic signal that in analytical chromatography is simply used to quantitate the amount of solute present, or qualify the presence or absence of a particular component in the mixture. Because of the greatly improved performance of using high pressure pumps through packed columns of very small particles, the modern technique has become known high performance liquid chromatography or HPLC.

Preparative high performance liquid chromatography extends the art of analytical liquid chromatography by adding a collection step to the instrument system. In this case, the electronic signals generated by one or more detectors are used to trigger the collection of specific segments of the mobile phase flowstream that contain the desired solutes. By isolating only these specific desired flow segments, a purification is performed which competes economically with other purification methods such as recrystallization. In order to be efficient, preparative HPLC systems must be scaled up to significantly higher flow rates, solute concentrations and column sizes in order to process significant amounts of material.

The solute concentrations used in preparative HPLC are disproportionately high compared to analytical HPLC. For example, a typical analytical HPLC separation may apply 5 microliters ($\mu$l) of sample mixture to the analytical separation column in a mobile phase flowstream of 1 mL/min. The solute concentrations of the mixture are typically in the range of 100 $\mu$g/mL, so a total of 500 nanograms are applied into the system. Further, it is common to split only a fraction ranging from 5% to 35% of the analytical mobile phase directly to the split detector. In contrast, users frequently inject 100 mg samples in one to two milliliter volumes into preparative HPLC systems scaled to only 20 times the column size and flow rate of the analytical system. Thus while the applied sample mass increases up to 200,000 fold and sample volume increases by 200 fold, the flow rates only increase 20 fold over the analytical separation. This means that local concentrations are as much as 1000 times higher in the preparative experiment. This presents a serious problem since the vast majority of electronic detectors for chromatography are designed for use with analytical concentrations of solutes.

The commercial solution to this problem of very high solute concentrations in preparative HPLC mobile phases is to use a flow splitting device to partition off a very small fraction of the main chromatographic flow stream, apply a diluent and deliver the diluted sample stream to a detector such as a mass spectrometer. Most manufacturers of preparative equipment supply a flow splitter for this reason. In practice, such splitting schemes can typically provide split ratios as high as 10,000:1 and dilute samples up to 100 fold.

The application of conventional flow splitters has been largely unsuccessful in preparative supercritical fluid chromatography (SFC) applications. In SFC, a gas such as carbon dioxide ($CO_2$) is compressed to liquid-like densities and used as the major component of the chromatographic mobile phase. Carbon dioxide has a critical temperature of 31 degrees Celcius and critical pressure of 73.8 bar. When raised above the critical temperature and pressure, $CO_2$ is no longer considered a liquid, but rather a supercritical fluid that has liquid-like densities and solvating power. The solvating power can be greatly enhanced by addition of organic liquids in solution with the $CO_2$. Use of varying compositions of $CO_2$ and methanol, for example, give a range of solvent strength from approximately hexane for pure $CO_2$ to nearly that of pure methanol in a 50% solution of Methanol/$CO_2$.

The advantages of preparative SFC are numerous and include faster separation, higher loading capability and lower energy requirements for the desolvation of collected fractions. Faster separation is achieved principally due to the significantly lowered viscosity of the SFC mobile phase. Unlike HPLC where water is the principle component with a viscosity of ~1 centipoise (cp) under standard conditions, supercritical $CO_2$ has a viscosity of ~0.05 cp at standard conditions of 100 bar and 40 deg C. The result from a chromatography standpoint is much lower pressure across separation columns even at high flow rates and much greater diffusion rates into and out of the columns separating medium. Since diffusion is the major rate limiting property of the chromatographic process, the entire separation process speeds up as much as 20 fold compared to similar HPLC separations.

Preparative SFC systems require a high pressure backpressure regulator to maintain the $CO_2$ at liquid-like densities that keep it soluble with organic liquids and solutes. Typically the backpressure setting ranges from 100 bar to 300 bar.

The mobile phase of SFC is subject to phase change, including up to a 500-fold volume expansion and significant temperature drop as the pressure goes from 100 bar to atmospheric pressure as it passes through traditional restrictor-based flow splitters prior to entry into the detector. This localized change of phase, flow, temperature and viscosity within the splitter restrictor makes the split behavior unpredictable, especially over the range of compositions and concentrations found during gradient chromatography. Further, the low diameter tubing required is subject to plugging, especially when the evaporating $CO_2$ carries with it some of the organic solvent solvating the solutes in the mobile phase. This evaporative solvent loss coupled with the intensely cold temperatures can easily result in precipitation of solutes from the remaining organic solvent in the tubing.

Construction of a useful flow splitter must take into account the physical properties of the mobile phase that is to be sampled. Such properties may include, for example, the flow rate, viscosity, phase (e.g. gas, liquid, supercritical), pressure, or composition variation (change in concentration of solvent, change in solutes eluted) over time. Each of these elements may affect the performance of the flow splitter. In addition, the flow and concentration requirements of the target detector or detectors must be taken into account.

What is needed is a flow-splitting device that can reliably control the split ratio from a primary flowstream from moderate to very high split ratios while diluting sample concentrations to levels appropriate to the target detectors. At the same time such a device must overcome the problems associated with fixed splitters including the effects of pressure and viscosity variations and phase change in the region where the actual flow splitting occurs. Finally, the device must be able to operate in a continuous manner at maximum pressures higher than 100 bar, for example up to about 300 bar, and eventually deliver the split flow to an atmospheric pressure device. The device should be suitable for both HPLC and SFC type mobile phases.

SUMMARY OF THE INVENTION

In one aspect, the present invention provides a splitter for a pressurized primary flowstream of a mobile phase. The splitter comprises:
   a first splitting stage that divides the primary flowstream between a major split flowstream and a minor split flowstream by means of a first and a second restrictive flow element;
   a first dilution stage that combines a dilution flow source with the minor split flowstream to create a diluted minor flowstream;
   a second splitting stage that divides the diluted minor flowstream between a secondary major diluted flowstream and a secondary minor diluted flowstream by means of a third restrictive element in the secondary minor diluted flow stream; and
   a second dilution stage wherein a conditioning flow source conditions the secondary minor diluted flow stream after the third restrictive element prior to outlet of the secondary minor diluted flowstream from the splitter.

In another aspect, the present invention provides a splitter for a pressurized primary flowstream of a mobile phase, the splitter comprising:
   a first splitting stage that divides the primary flowstream between a major split flowstream and a minor split flowstream by means of a first and a second restrictive flow element;
   a first dilution stage that combines a dilution flow source with the minor split flowstream to create a diluted minor flowstream;
   a second splitting stage that divides the diluted minor flowstream between a secondary major diluted flowstream and a secondary minor diluted flowstream by means of a third restrictive element in the secondary minor diluted flow stream;
   a second dilution stage wherein a conditioning flow source conditions the secondary minor diluted flow stream after the third restrictive element prior to outlet of the secondary minor diluted flowstream from the splitter; and
   a pressure balancing stage which recombines the major split flowstream and the secondary major diluted flowstream of the first and second splitting stages to an exit flowstream in fluidic communication with a backpressure regulator.

These and other aspects of the present invention will become more readily apparent from the following drawings, detailed description, and appended claims.

BRIEF DESCRIPTION OF THE DRAWINGS

For a better understanding of the nature of the present invention, its features and advantages, the subsequent detailed description is presented in connection with accompanying non-limiting drawings in which.

DETAILED DESCRIPTION OF THE INVENTION

Figure 1:
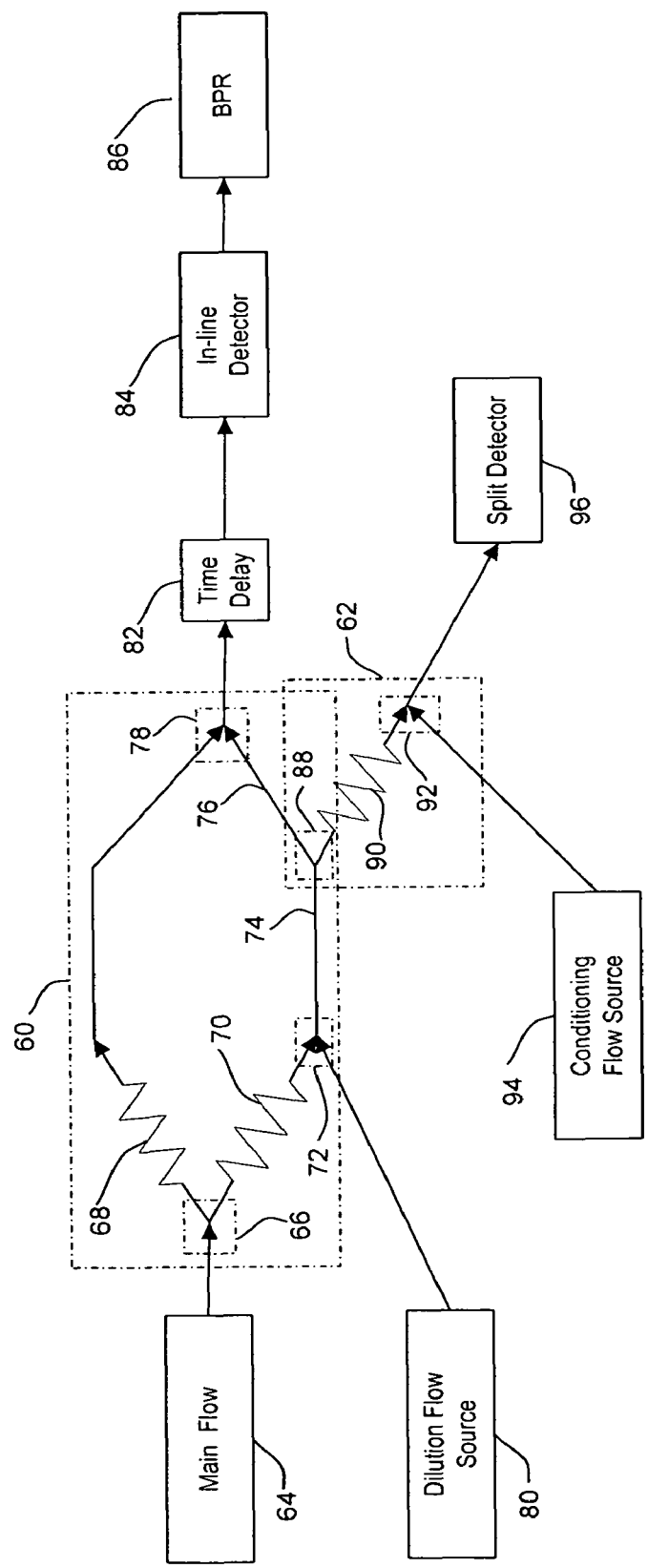
FIG. 1 is a diagram of an embodiment of the invention with a pressure balanced first splitting stage, a first dilution stage, a second pressure controlled splitting stage, and a second dilution stage.

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

All stated pressure units are gauge pressure.

The present invention is directed to a high split ratio flow splitter that can handle the flow characteristics of typical HPLC mobile phases and pressures as well as the extended range of pressures, viscosities and phase transitions associated with supercritical fluid chromatography mobile phases. With minor changes in the components, flow splitters of the present invention can handle main flow rates from 1 mL/min to 1000 mL/min. Conventional single-stage flow splitters achieve splits up to about 20,000:1 for a preparatory flow rate of 50-100 mL/min., whereas splitters of the present invention can achieve split ratios of well over 1,000,000:1.

As will be understood by one skilled in the art, the mobile phase in supercritical fluid chromatography may experience a change in state over the course of the chromatography due to variations in temperature and/or pressure through the system. Thus, in the case of $CO_2$, for example, a $CO_2$ mobile phase may exist as a highly compressed and liquified gas, a supercritical fluid, or as a low viscosity, compressible fluid at different stages of the preparation. As used herein, therefore, the term "supercritical fluid" will refer to those compounds that do exist or can exist in the supercritical fluid state during chromatography, regardless of the actual state of the compound at any particular point in time during chromatography and collection.

In addition to $CO_2$, other compounds useful in SFC include, but are not limited to, ethane, propane, nitrous oxide, butane, isobutene, sulfur hexafluoride, water, hydrochlorofluorocarbons, hydrofluorocarbons, alkanes, or any combination of these.

As would also be understood by one skilled in the art, the mobile phase in SFC optionally includes an organic liquid solvent. Suitable organic solvents include, for example, lower alcohols such as ethanol, methanol, 2-propanol, isopropanol, n-butanol as well as a variety of less polar solvents such as acetonitrile, dioxane, methylene chloride and the like.

The mobile phase in standard HPLC implementations using the flow splitter of the present invention may comprise, for example, water, aqueous buffers, acetonitrile, and alcohols for the most common use of this technique.

In one embodiment, the present invention is a passive restrictor network comprised of one or more alternating stages of flow splitting and dilution that occur serially in the split flowstream. Preferably, there are at least two or more flow splitting and dilution stages. Together, the serial stages reduce the total absolute contribution and relative concentration of solutes from the main flow stream that are transferred to the final electronic detector. As used herein, the term "passive" in connection with restrictor means that the restrictor is not electronically controlled.

Tunability of the splitter is achieved hydraulically, by increasing or decreasing one or more dilution flows into the splitter to change both dilution and split ratio values. Pressure balancing within the system, in addition to a backpressure regulator, dramatically attenuates variation of the splitter performance in the presence of significant changes in pressure, viscosity and density and flow rate in the mobile phase.

For example, effective split ratios for 100 mL/min flow systems can range from 1000:1 to well over 2,000,000:1, while effective dilution of the main stream concentration can range from 50:1 to over 10,000:1. Desired split ratios for this flow rate are approximately 200,000:1 with dilution >1000:1. Since the flow rate for preparative SFC can range from 2 mL/min. to 2,000 mL/min., the split ratios will vary depending on the flow rate. Splitters of the present invention can operate with primary flow rates of a minimum of 2 mL/min., 10 mL/min. or 12.5 mL/min., anywhere up to flow rates of 800 mL/min., 1,000 mL/min., or 2,000 mL/min., depending on the needs of the user.

In one embodiment, the main flow which exits the separation column is first split by a balanced flow restrictor pair into major and minor flowstreams. To isolate the splitting behavior of this first splitting stage from pressure variations in the downstream portion of the flow path, the major and minor flowstreams are eventually rejoined at the exit of the first splitter. This insures that the downstream pressure regulation will affect both restrictors of the splitter equally. In addition, a minimum pressure of about 100 bar is maintained at the outlet of the first splitting stage to insure that SFC mobile phase components remain at their liquid-like densities.

At the first dilution stage, addition of a dilution flow in at least 90% excess to the minor split flow of the first splitting stage creates a flowstream that has essentially the same physical properties of the dilution solvent and is relatively independent of the properties of the main flow stream mobile phase components. Thus, even if the main mobile phase changes dramatically in composition or viscosity, the composition of the diluted split flowstream remains virtually constant in these parameters. This permits all subsequent splitting stages of the invention to be performed using traditional pressure-based, resistive flow splitting techniques.

In general, the dilution flow rate will vary depending on the main flow rate. For example, for a 100 mL/min. main flow rate, a desirable dilution flow rate would be from 0.5 to 20 mL/min., more preferably between 0.5 to 5 mL/min. A minimum flow rate must be maintained to prevent back flow from the major flowstream into the minor flowstream via the pressure balancing tee of the the system. The maximum dilution flow rate can be up to 20% of the main flow rate.

An embodiment of the invention is displayed in FIG. 1. In this embodiment, two splitting and dilution stages, 60 and 62, are used to reduce the fractional contribution of the main flowstream and the absolute concentration of solutes that enter split detector 96. Main flow source 64 enters a first splitting and dilution stage 60 which is comprised of splitting tee 66; restrictive flow elements 68 and 70; mixing tee 72; low restriction flow conduits 74 and 76 and pressure balancing tee 78. As the main flow enters splitter and dilution stage 60, it is split into major and minor flowstreams flowing respectively through restrictors 68 and 70. Dilution flow source 80 provides additional solvent flow to the minor flowstream at mixing tee 72 and this combined flowstream passes in majority through conduits 74 and 76 to pressure balancing tee 78 where it recombines with the major flowstream and exits the splitter. Main flow continues through a variety of optional flow elements such as time delay element 82 and in-line detector 84 to eventually reach backpressure regulator (BPR) 86, which maintains the upstream flow at an elevated pressure.

Pressure balancing tee 78 of the first splitting and dilution stage 60 has a major effect on the performance of the splitting function. By recombining the major and minor split flows at this point, the pressure drop across restrictors 68 and 70 becomes a function only of the pressure drop across the splitter stage itself and not the absolute pressure of the flowstream. As a result, a relatively small pressure drop of 3 to 30 bars across the restrictors can be achieved, even in the case where the backpressure regulator is elevating the flowstream to hundreds of bars of absolute pressure. This feature is particularly important in the case of SFC mobile phases, since pressure tee 78 maintains the outlet end of split restrictor 70 at the high pressure controlled by the BPR. This prevents the liquefied gas portion of the mobile phase from changing phase in the splitter and creating unpredictable splitting behavior as well as poor mixing with the dilution solvent at mixing tee 72. Further, by providing a smaller pressure drop across restrictor 70, a wider selection of capillaries are commercially available to create split flows in the most desirable 10 to 500 μL/min range for flow through restrictor 68 of the low viscosity mobile phase.

In addition, pressure balancing the first splitter minimizes the effect of the physical properties of the mobile phase on the split ratio. For cases where flow restrictors 68 and 70 respond similarly in pressure drop to changes in viscosity, density or flow rate, the split ratio remains constant, since both branches of the split flow experience the same change at the same time. An example of such behavior is found in a pair of laminar flow tubular restrictors, which are governed by the Hagen-Poiseuille relationship in equation 1:

$$F=(\Delta p \pi r^4)/(8L\eta) \quad (1)$$

where F is the flow rate through the tubing; $\Delta p$ is the pressure drop along the tubing; r is the radius of the tubing; L is the tubing length and $\eta$ is the fluid viscosity. The equation can be rewritten in terms of pressure as shown in equation 2.

$$\Delta p=(8L\eta F)/(\pi r^4) \quad (2)$$

From equation 2 it can be seen that changes in flow have a direct proportional effect on the $\Delta p$ across a laminar restrictor. Further, in the balanced flow splitter of FIG. 1, the pressure drop across restrictors 68 and 70 are kept the same due to pressure balancing tee 78, so long as conduits 74 and 76 are sized to offer low relative pressure drop despite the added flow from dilution source 80. For example, for methanol, with a flow rate of up to 10 mL/min., a 20 cm length tube of 500 μm inner diameter (id) is sufficient and does not cause a significant pressure drop. Since the same $\Delta p$ can only be achieved if the flow change is proportional in each restrictor, the ratio of flows will remain constant for any flow change in the system.

In a similar manner, changes in viscosity of the mobile phase stream will cause proportional changes of $\Delta p$ across each restrictor. It should be noted that restrictors 68 and 70 contain only mobile phase from the main flowstream. This is despite dilution of the minor flow stream at mixing tee 72 which is downstream. Further, residence time in these restrictors is short, on the order one second or less. At any time the fluid viscosity is the same in each of the two restrictors 68 and 70. The result is that as viscosity changes in the mobile phase, the pressure drop across both restrictors of the first splitter adjust again without affecting the split ratio.

The split ratio for splitter 60 is calculated as the ratio of flows though the major and minor flow restrictors 68 and 70 respectively as shown in equation 3 where constant terms have been represented by $\kappa$.

$$F_1/F_2=\kappa(\Delta p_1/\Delta p_2)(\eta_2/\eta_1)(r_1/r_2)^4(L_2/L_1) \quad (3)$$

As described above for the first splitting and dilution stage, $\Delta p_1=\Delta p_2$ and $\eta_1=\eta_2$ so equation 3 reduces to final two ratios of tubing radius and length. The radius ratio is to the fourth power so a small change in radius will have a dramatic on the relative flows.

The invention does not require that restrictors 68 and 70 be of the same type. For example, in cases where very small internal volumes are necessary to insure rapid transport of very small flows, a laminar flow capillary tube might be the best solution. On the other hand, in cases where very large flows exist, or timing is not as critical, another type of restrictor may be employed. The only requirement is that the restrictors vary in $\Delta p$ in generally the same manner with changes in the composition of the mobile phase. For example, a laminar flow restrictor may be matched with a restrictor of any type that increases in pressure drop in a generally linear manner with viscosity. One example of such an alternate restrictor is a porous bed restrictor which varies according to Darcy's Law shown in equation 4, $$F=\kappa A\Delta p/(L\eta) \quad (4)$$

where F is the flow rate through the tubing; $\kappa$ is a permeability factor; A is cross sectional area of the bed, $\Delta p$ is the pressure drop along the bed; L is the bed length and $\eta$ is the dynamic viscosity. Comparison of equations 1 and 4 shows that the variation of key parameters such as pressure drop, length and viscosity are similarly related to flow and as such should allow the two different restrictors to balance one another and provide a constant split ratio despite changes in fluidic composition or flow. As with identical type restrictors, the two restrictors must be matched to provide appropriate flow through restrictor 70. In one embodiment this flow will be <500 μL/min to allow a minimum 10:1 dilution of the split flow with a 5 mL/min dilution flow source such as a standard analytical pump. Other suitable restrictors include orifice restrictors and active resistors.

The pressure balancing tee 78 provides a low restriction path for excess dilution flow from source 80. As higher flow rates are delivered to mixing tee 72, the dilution ratio increases. If conduits 74 and 76 are sized properly to cause minimal pressure drop, the dilution ratio may be changed over a very wide range without affecting the split flow from restrictor 70 or downstream split flows discussed below. This provides the first splitter stage with the capability of adjusting the dilution ratio by simply increasing or decreasing dilution flow from source 80. Such adjustability provides a facile way of tuning the splitter to handle a much wider range of analyte concentrations in the main flowstream.

Second splitting and dilution stage 62, which overlaps with first splitting and dilution stage 60, is comprised of inlet conduit tube 74; splitting tee 88; flow conduit 76; restrictive flow element 90; and mixing tee 92. This second splitting stage operates very differently from the primary splitting stage described above. First, the fluid in inlet tube 74 is the result of a significant dilution of the original mobile phase composition. So long as this dilution is at least 10:1, the composition of fluid contained in conduit 74 is essentially constant, with physical properties very closely resembling the dilution solvent despite any changes arising in the main mobile phase composition. In practice, dilution ratios of 10:1 to 200:1 are desirable in this stage, more preferably 10:1 to 50:1, for a 5 mL/min. flow rate, which makes the contribution of the main mobile phase even lower.

Splitting tee 88 divides the flow into two streams. The major flowstream is typically conduit 76 which rejoins the main flowstream at pressure balancing tee 78 and communicates the pressure from backpressure regulator 86 back to splitting tee 88. It is the pressure at splitting tee 88 that determines the flow through restrictor 90, and thereby the split ratio of this stage. In the embodiment shown in FIG. 1, restrictor 90 delivers flow to mixing tee 92 at nearly atmospheric pressure. Hence, the $\Delta p$ across restrictor 90 will be the same as the gauge pressure measured at pressure balancing tee 78. Further, this pressure will typically be determined by the setting of BPR 86. For HPLC systems this value may be up to a few hundred psi. In supercritical fluid systems, the value will typically be in excess of 100 bar [1450 psi] up to 300 bar, to maintain the supercritical components at a liquid-like density. Preferably, the pressure is maintained between 100-200 bar. As a result, restrictor 90 must be sized based on prior knowledge of the backpressure range to be used.

As a general goal, flow through restrictor 90 should be limited to allow sufficient additional dilution within the flow range of the split detector. It should be noted that the effects of phase transition of supercritical components are very minor at this point due to the high dilution of the prior step. Gaseous components will typically remain dissolved within the organic liquid at ratios of 50:1 or greater under even under these conditions. Since the composition of fluid entering splitter tee 88 is relatively constant, the minor split flow through restrictor 90 can be calculated from equation 1.

Flow exiting restrictor 90 enters mixing tee 92 where it combines with conditioning flow from source 94. The conditioning fluid may contain chemical reagents such as buffers to induce ionization of the target solutes in solution in order to achieve a particular type or level of ionization in split detector 96. Flow from conditioning flow source 94 will also add further dilution to the detector flowstream. The total flowrate that leaves mixing tee 92 is limited by the flow requirements of split detector 96. As an example, it is common for mass spectrometer detectors to limit flow to 1 mL/min for certain common ionization probes to perform properly.

Both the dilution flow source and the conditioning flow source are tuned (as to flow rate and composition) by means of an electronic controller (not shown).

Attempting to split flows by more than about 20,000:1 in a single stage may introduce problems of time delay and allow unswept volumes within the flow system to contribute to distortion of the split flowstream composition. A splitter that uses more than one stage of splitting and dilution can be easily assembled without the same issues. In a first stage, a 2,000:1 split and 100:1 dilution is achieved. Now, a second stage of splitting and dilution is performed on the split flow stream with 100:1 split ratio and 20:1 dilution. The effective split ratio from the two stages is 200,000:1. The effective dilution ratio of the two dilution steps is 2000:1.

In this example, for a 100 mL/min main flow, each split restrictor, 70 and 90 respectively, would carry 50 µL/min flow. Since the volume of restrictors 70 and 90 typically is much than 1 µL, the timing delay of this process can be maintained at under 2 seconds which compares favorably to the very difficult, multi-second process of creating a single split flow of 0.5 µL/min [e.g. 200,000:1 split ratio] diluted with 999.5 µL/min of dilution solvent. Restrictor flow rates used in the consecutive stages of splitting and dilution approach are 100 times larger than single stage splitting flows and offer continuous washing of the flow system to avoid significant peak distortions due to poorly swept flow regions.

An example of a specific implementation of the present invention for preparative chromatography using standard solvents is as follows:

For a main flow of 50 mL/min (flow from the HPLC), a 100 cm length of 500 µm id tubing is used as restrictor 68 and a 35 cm length of 75 µm id tubing is used for restrictor 70. In this case, the split ratio would be calculated from equation 3 as 691:1, with 72 µL/min passing through restrictor 70 and the remaining flow passing through restrictor 68. The calculated pressure drop across this first splitting stage would range from approximately 80 psi [5.5 bar] for pure water to 30 psi [2.1 bar] for pure acetonitrile which are the typical HPLC mobile phase solvent components. Further, the dilution ratio of the minor flowstream for this stage, assuming addition of 5 mL/min from dilution flow source 80, would be 70:1. For the second stage, where methanol is used as the first dilution solvent and the $\Delta p$ is 145 psi [10 bar], a selection of a 20 cm length of 40 µm id tubing for restrictor 90 allows a flow of approximately 34 µL/min. This produces a split ratio of 151:1 for the second splitting stage. Addition of a final conditioning flow of 0.966 mL/min gives a secondary dilution of ~30:1.

Final determination of split and dilution ratios is achieved by calculating the product of sequential split or dilution steps. From the example given, the final split ratio would be the product of 691 for the first stage and 151 for the second split stage for a total split ratio of ~104,000:1. Thus less than 0.001% of the original injected sample enters the split detector. For a 100 mg sample this would be less than 1 µg delivered to the detector. Similarly, serial dilutions of 70 and 30 fold produce a final dilution of ~2100:1 or ~0.05% of the solute concentration. These conditions allow a solute of 10 mg/mL emerging from the separation column to enter the split detector at less than 5 µg/mL concentration. This is a much more appropriate concentration for analytical detectors such as mass spec or ELSD detectors. Finally, if flow delays through the restrictors are calculated, the conditioned sample is delivered to split detector within 0.1-5 seconds of entering the splitter, more preferably within 0.1-2 seconds. Such short delays at this high dilution are not possible using conventional single stage splitting and dilution techniques without severe distortion of peak shape.

Only minor adjustment is required for SFC systems using $CO_2$ at, for example, 50 mL/min. Adjustments must be made to account for the lower viscosity of the mobile phase and much higher backpressure of the flow system. For this system, restrictor 68 is typically selected to provide a pressure drop of between 30-120 bar for the highest viscosity flow which is approximately 0.3 cP at 50% methanol composition. In this case, selection of restrictor 70 as a 30 µm id by 20 cm long capillary tube allows 60 µl/min flow or a split ratio of 838:1. When 5 mL/min of dilution flow from source 80 is added the dilution ratio is 85:1. Pressure balancing tee 78 set at a typical level of 100 bar or higher insures no outgassing of supercritical components during this splitting stage. The second stage in this system follows equation 1 for flow through restrictor 90. Hence a restrictor of 25 µm id and 25 cm length will provide ~41 µl/min flow of methanol when the BPR is set to 100 bar. The split ratio of this stage is 123:1. Addition of 1 mL/min conditioning flow further dilutes the second split flow by 52:1. As a result, the total split and dilution ratios can be calculated to be 103,000:1 and 2150:1 respectively, which is very similar to the HPLC case.

Table 1 below provides additional examples of specific implementations for both SFC and HPLC systems.

Due to the very high dilution of the splitter in each case, the split detector receives virtually identical compositions from each system (HPLC and SFC) and should get identical results. Thus the splitter also provides the benefit of making the measurement independent of original flow source. This is not the case for traditional SFC vs. HPLC splitting devices measured by mass spec, where differences in ionization and suppression levels are frequently found.

The embodiment of the splitter shown in FIG. 1 is suitable for incorporation into any preparative chromatograph control system. For example, signals from a mass spectrometer in the split detector position and from a UV detector in an in-line position can be used to signal the presence of a solute in the main flowstream just before it reaches the collection system. For purposes of timing, the time delay element 82 may be placed either before or after in-line detector 84 depending on the time required by the controller to respond to the trigger signals and initiate collection. Timing delays should be minimized between the time solute from the main flowstream exits the splitter at tee 78 and the time the conditioned split flow reaches the split detector. This prevents the need for long delays in the flow stream which can degrade the separation efficiency of the system. A general target of less than 5 seconds delay here is sufficient for typical operation, but performance can be improved further with shorter delay times, for example between 0.1 to 2 seconds.

Figure 2:
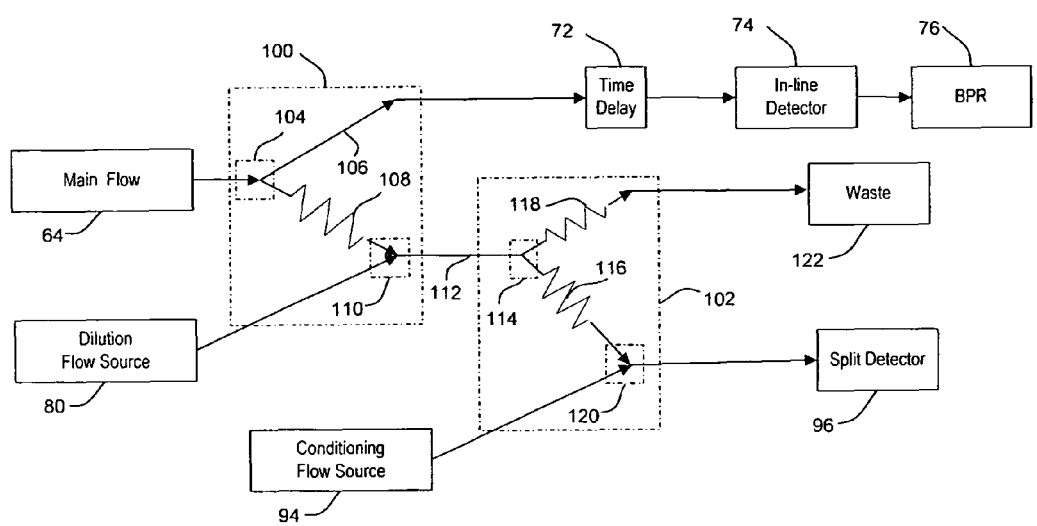
FIG. 2 is a diagram of another embodiment of the invention without pressure balancing.

An additional embodiment of the invention is disclosed in FIG. 2. Like FIG. 1, the embodiment has two split and dilution stages 100 and 102 respectively to serially dilute a portion of the main flowstream for split detector 96. The significant difference between these embodiments is the lack in FIG. 2 of the pressure balancing tee 78 shown in FIG. 1. Removal of the pressure balancing tee eliminates the automatic compensation in the first splitter stage 100 for changes in flow, viscosity and pressure. As a result, this stage will vary more widely in performance over the course of a standard gradient separation common to HPLC and SFC systems. Further, these factors (flow, viscosity and pressure) must be manually calculated in the design of the splitter and will limit its operation to a smaller dynamic range than the embodiment shown in FIG. 1.

Nevertheless, FIG. 2 preserves a benefit of serial splitting and dilution that permit the splitter to handle high concentrations of analytes as found preparative chromatography flowstreams. In FIG. 2, splitting and dilution stage 100 is comprised of splitting tee 104; main flow conduit 106; split flow restrictor 108; and mixing tee 110. The splitter receives flow from main flow source 64 which divides into major and minor flowstreams flowing through conduit 106 and restrictor 108 respectively. Dilution source 80 supplies dilution solvent at mixing tee 110 to reduce the concentration of solutes in the flowstream. The diluted flow stream is passed to splitting and dilution stage 102 via conduit 112.

Second splitting and dilution stage 102 is comprised of splitting tee 114; restrictors 116 and 118 and mixing tee 120. Flow enters this stage via conduit 112 and is split into major and minor flowstreams through restrictors 116 and 118 respectively. Restrictor 118 carries excess diluted flow to waste 122 or alternately to a second split detector in the flow system (not shown). Split flow from restrictor 116 is diluted at mixing tee 120 by conditioning flow 94, then delivered to primary split detector 96.

A difference in the operation of this splitter from that of FIG. 1 is the nonlinear behavior of splitting and dilution based on the fluidic network. First, due to the absence of the pressure balancing tee, there is no need to add a balancing restrictor in conduit 106 of the main flow stream since the backpressure regulator will be the dominant restrictor determining the pressure drop across split restrictor 108. Flow through restrictor 108 will be viscosity dependent which means that the split ratio will vary in stage 100 during a gradient chromatography separation. Second, unlike the embodiment in FIG. 1, flow from dilution source 80 is restricted downstream. As a result, if flow is increased, a higher pressure drop will result across second stage 102 and the pressure drop across restrictor 108 will decrease. Thus increasing flow of the dilution source will result in a greater dilution than in the embodiment shown in FIG. 1 since this will cause a reduction of split flow at the same time. This nonlinear change in dilution will continue until the pressure drop across restrictor 108 becomes zero at which time only minor diffusional flow will cross mixing tee 110. Increasing dilution flow from this point will cause the restrictor to reverse its flow direction and backflush dilution solvent into the main flowstream. No further solute signal will be received at the split detector under this condition.

In the case of SFC systems, restrictors must be selected to maintain a high enough backpressure on the output of splitting stage 100 to prevent outgassing of the supercritical components. This needs to be done along with predetermination of the minimum flow from the dilution source so that some range of dilution source tuning can be achieved. The splitter may also require the backpressure regulation of the system to be increased (as compared to the embodiment shown in FIG. 1) for both HPLC and SFC cases to insure sufficient pressure drop across both stages.

Figure 3:
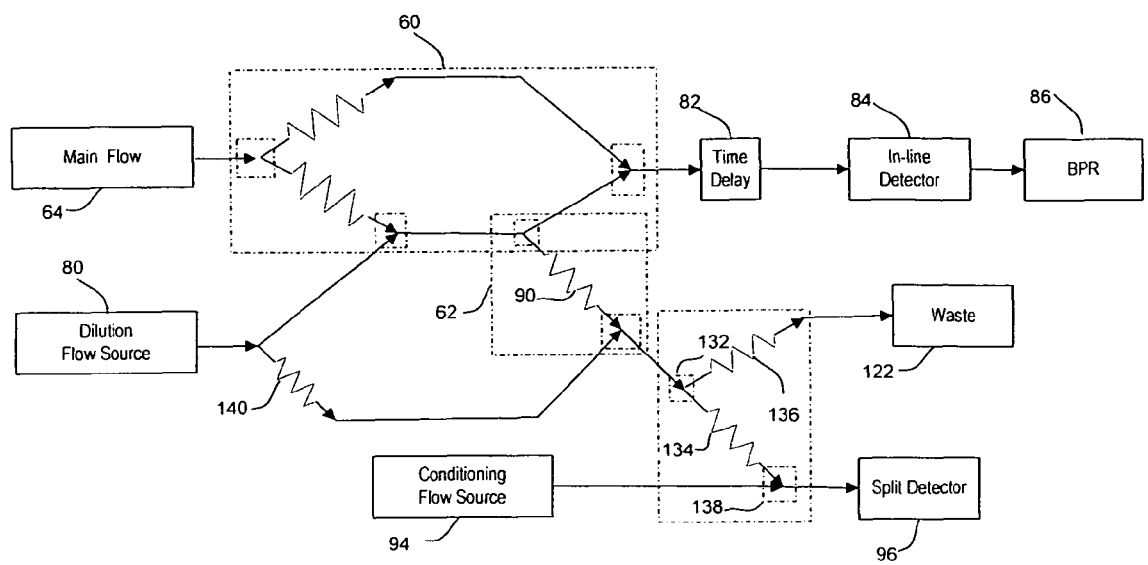
FIG. 3 is a diagram of another embodiment of the invention with multiple serial splitting and dilution stages.

FIG. 3 displays an embodiment with three splitting and dilution phases. In this figure, split and dilution stages 60 and 62 act as described in FIG. 1. The minor stream of split and dilution stage 62 in this case delivers to third split and dilution stage 130 rather than directly to the split detector 96. Stage 130 is comprised of splitting tee 132, flow restrictors 134 and 136 and mixing tee 138. A waste receptacle 122 receives flow diverted through restrictor 136.

Like the stage 62, splitting and dilution stage 130 requires a pressure drop across the restrictor network to operate. However, this may be quite small, on the order of a few bars, and should not interfere with significantly with the larger pressure drops in upstream stages. As a result, the first two stages experience little effect from the addition of the third stage.

The dilution flow scheme of FIG. 3 is also worthy of note. In this case a single dilution source, 80, supplies dilution solvent to both stages 60 and 62. This is accomplished by addition of restrictor 140 which limits dilution flow to stage 62 based on the back pressure from BPR 86. Hence for calculation purposes, the dilution flow received into the first stage will be total flow minus the flow through restrictor 140. Since both dilution flow and split flow through restrictor 90 are governed by BPR 86, they will vary proportionately with changes of the BPR. As a result, the dilution ratio will remain constant in this case. If desired, a separate flow source such as a pump may be used for dilution at stage 62 if more direct control is required.

Typically, a third stage such as stage 130 would be implemented to allow more overall dilution of the main stream before reaching the detector. In this case, flow from a second dilution source such as conditioning flow 94 could be increased without regard of the split detector capacity to yield a higher dilution. The advantage of serial dilution over three steps also allows a far greater range and efficiency. For example three serial dilutions of 10 µl/min split flows to 1 mL/min total flow [e.g. 100:1 dilutions] would yield a final 1,000,000:1 final dilution while consuming less than 3 mL/min of dilution flow. This is substantially less solvent than would be required with one or even two stages of dilution. This example shows the extensibility of adding further splitting and dilution stages to the invention to achieve very high dilution ratios.

For all examples given, while the discussion has been focused on the use of real-time serial splitting and dilution for chromatographic purposes, it can readily be applied by one skilled in the art to any pressurized flowstream containing solutes outside the range of standard electronic detectors. The use of the invention with supercritical mobile phases relies on the first splitting and dilution stage occurring at high pressure to retain the supercritical component at liquid like density during the splitting operation. Thereafter, with at least 10:1 dilution, diluted split flowstreams may be treated essentially as having the properties of the diluent and need receive no special treatment due to their supercritical states. The invention may also easily be applied to process streams as well as liquid or supercritical fluid extraction flowstreams. Further, the invention may be used to monitor reaction progress in recirculated flowstreams from automated reaction systems.

TABLE 1

| Case | Type | Flow mL/min Max | Flow mL/min Min | Viscosity cP Max | Viscosity cP Min | delta P bar Max | delta P bar Min | Restrictor 68 | Restrictor 70 | Restrictor 90 | Split Ratio Min | Split Ratio Max | Dilution Ratio Min | Dilution Ratio Max |
|---|---|---|---|---|---|---|---|---|---|---|---|---|---|---|
| 1 | typical use | SFC | 100 | 100 | 0.3 | 0.08 | 32 | 8.5 | 10 mm × 10 mm packed bed | 30 um × 10 cm tube | 20 um × 10 cm tube | 21,200 | 103,000 | 66 | 2,800 |
| 2 | full range | SFC | 50 | 200 | 0.56 | 0.07 | 120 | 3.8 | 10 mm × 10 mm packed bed | 30 um × 10 cm tube | 20 um × 10 cm tube | 10,600 | 812,213 | 11 | 4,220 |
| 3 | high range | SFC | 200 | 800 | 0.56 | 0.07 | 120 | 3.8 | 20 mm × 10 mm packed bed | 30 um × 10 cm tube | 20 um × 10 cm tube | 42,000 | 12,900,000 | 11 | 16,800 |
| 4 | low range | SFC | 12.5 | 50 | 0.56 | 0.07 | 120 | 3.8 | 5 mm × 10 mm packed bed | 30 um × 10 cm tube | 20 um × 10 cm tube | 2,600 | 51,700 | 11 | 1,080 |
| 5 | HPLC use | HPLC | 25 | 100 | 1 | 0.3 | 100 | 7.5 | 250 um × 60 cm tube | 30 um × 10 cm tube | 40 um × 40 cm tube | 12,800 | 387,000 | 12 | 7,650 |

Assumptions

| Ranges | Min | Max |
|---|---|---|
| Dilution flow | 0.5 | 20% of main flow |
| Conditioning flow | 0.05 | 1 |

1. Split and dilution ratios are calculated based on equation 1 of patent (laminar tube flow)
2. Highest split ratio is at highest flow [main, dil, cond]
3. Lowest split ratio is at lowest flow [main, dil, cond]
4. Highest dilution is at highest dilution and cond flows; lowest main flow
5. Lowest dilution is at lowest dilution and cond flows; highest main flow
6. data at 100 bar BPR setting
7. intend to use restrictors ranging from 20 um to 63 um id and 10 cm to 100 cm length
8. Viscosity range for SFC is pure CO2 to pure methanol
9. Viscosity range for HPLC is pure H20 to pure acetonitrile
10. packed bed pressure drop determined experimentally with 10 mm × 10 mm column and extrapolated to other ranges

What is claimed is:

1. A splitter for a pressurized primary flowstream of a mobile phase, comprising:
   a first splitting stage that divides the primary flowstream between a major split flowstream and a minor split flowstream by means of a first and a second restrictive flow element;
   a first dilution stage that combines a dilution flow source with the minor split flowstream to create a diluted minor flowstream;
   a second splitting stage that divides the diluted minor flowstream between a secondary major diluted flowstream and a secondary minor diluted flowstream by means of a third restrictive element in the secondary minor diluted flow stream; and
   a second dilution stage wherein a conditioning flow source conditions the secondary minor diluted flow stream after the third restrictive element prior to outlet of the secondary minor diluted flowstream from the splitter.

2. A splitter for a pressurized primary flowstream of a mobile phase, comprising:
   a first splitting stage that divides the primary flowstream between a major split flowstream and a minor split flowstream by means of a first and a second restrictive flow element;
   a first dilution stage that combines a dilution flow source with the minor split flowstream to create a diluted minor flowstream;
   a second splitting stage that divides the diluted minor flowstream between a secondary major diluted flowstream and a secondary minor diluted flowstream by means of a third restrictive element in the secondary minor diluted flow stream;
   a second dilution stage wherein a conditioning flow source conditions the secondary minor diluted flow stream after the third restrictive element prior to outlet of the secondary minor diluted flowstream from the splitter; and
   a pressure balancing stage which recombines the major split flowstream and the secondary major diluted flowstream of the first and second splitting stages to an exit flowstream in fluidic communication with a backpressure regulator.

3. The splitter of claims 1 or 2, wherein the conditioning flow source contains chemical reagents to optimize detection of solutes at an electronic detector.

4. The splitter in claims 1 or 2, wherein one or more of the first, second or third restrictive flow elements are comprised of laminar flow tube restrictors.

5. The splitter in claims 1 or 2, wherein one or more of the first, second or third restrictive flow elements are comprised of porous bed restrictors.

6. The splitter of claims 1 or 2, wherein the mobile phase of the primary flowstream comprises a mixture of 1) a supercritical fluid, 2) one or more solutes and optionally, 3) one or more organic liquid solvents.

7. The splitter of claim 6, wherein the one or more organic liquid solvents is selected from the group consisting of ethanol, methanol, 2-propanol, isopropanol, n-butanol, acetonitrile, dioxane, methylene chloride and mixtures thereof.

8. The splitter of claims 1 or 2, wherein the mobile phase of the primary flowstream comprises a mixture of 1) solutes, 2) optionally, an aqueous buffer, and 3) one or more solvents selected from the group consisting of water, alcohols, acetonitrile and mixtures thereof.

9. The splitter of claims 1 or 2, further comprising:
   one or more controllers operatively connected to the dilution flow source and the conditioning flow source; and
   an electronic detector connected to the secondary minor diluted flowstream and operatively connected to at least one controller, wherein during active flow of the primary flowstream, the one or more controllers controls dilution of solute in the minor split flowstream and the secondary minor diluted flowstream, and the solute in the secondary minor diluted flowstream is analyzed by the electronic detector.

10. The splitter of claims 1 or 2, wherein the primary flowstream is within a chromatography system.

11. The splitter of claims 1 or 2, wherein the primary flowstream is within an extraction system.

12. The splitter of claims 1 or 2, wherein the primary flowstream is within a reaction system.

13. The splitter in claim 9, wherein the split ratio of the mass fraction of dissolved solutes in the primary flowstream to the mass fraction of dissolved solutes reaching the detector is between 50:1 and 5,000,000:1.

14. The splitter in claim 9, wherein the conditioned minor diluted flowstream is delivered to the electronic detector in 0.1 to 5 seconds from entry into the splitter.

15. The splitter of claim 2, further comprising:
   a third splitting stage that divides the secondary minor diluted flowstream between a ternary major and a ternary minor diluted flowstream by means of fourth and fifth restrictive elements in the ternary major and ternary minor flow streams;
   a waste receiver which receives flow from the fourth restrictive element of the ternary major flow stream; and
   a third dilution stage wherein a second conditioning flow source dilutes flow emerging from the fifth restrictive element;
wherein the ternary minor flow stream is delivered to the electronic detector.

16. The splitter of claims 1 or 2, wherein the splitter operates in an ambient pressure environment of between 100-300 bar.

17. The splitter of claims 1 or 2, wherein the flow rate of the primary flowstream is between 2 mL/min. and 2,000 mL/min.

18. The splitter of claims 1 or 2, wherein the flow rate of the primary flowstream is between 10 mL/min. and 1,000 mL/min.

* * * * *